(12) United States Patent
Datta et al.

(10) Patent No.: US 9,320,496 B2
(45) Date of Patent: Apr. 26, 2016

(54) VOLUMETRIC IS QUANTIFICATION FOR ULTRASOUND DIAGNOSTIC IMAGING

(75) Inventors: Saurabh Datta, Cupertino, CA (US); Seshadri Srinivasan, Santa Clara, CA (US); Christophe Duong, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 948 days.

(21) Appl. No.: 12/712,593

(22) Filed: Feb. 25, 2010

(65) Prior Publication Data

US 2011/0208056 A1 Aug. 25, 2011

(51) Int. Cl.
*A61B 8/00* (2006.01)
*A61B 8/06* (2006.01)
*A61B 8/08* (2006.01)
*A61B 8/13* (2006.01)

(52) U.S. Cl.
CPC . *A61B 8/483* (2013.01); *A61B 8/06* (2013.01); *A61B 8/13* (2013.01)

(58) Field of Classification Search
USPC .......................................................... 600/440
See application file for complete search history.

(56) References Cited

U.S. PATENT DOCUMENTS

| | | | | |
|---|---|---|---|---|
| 5,609,155 A | * | 3/1997 | Guracar | 600/453 |
| 5,623,930 A | * | 4/1997 | Wright et al. | 600/456 |
| 5,806,521 A | * | 9/1998 | Morimoto et al. | 600/447 |
| 5,840,018 A | * | 11/1998 | Michaeli | 600/300 |
| 5,908,391 A | | 6/1999 | Muzilla | |
| 6,030,344 A | * | 2/2000 | Guracar et al. | 600/447 |
| 6,293,914 B1 | * | 9/2001 | Sumanaweera et al. | 600/465 |
| 6,719,697 B2 | | 4/2004 | Li | |
| 7,229,412 B2 | | 6/2007 | Jacob et al. | |
| 7,299,140 B2 | | 11/2007 | Liu et al. | |
| 7,450,746 B2 | * | 11/2008 | Yang et al. | 382/131 |
| 8,094,893 B2 | * | 1/2012 | Roundhill et al. | 382/128 |
| 2003/0045797 A1 | | 3/2003 | Christopher et al. | |
| 2004/0102706 A1 | | 5/2004 | Christopher et al. | |
| 2005/0165308 A1 | | 7/2005 | Jacob et al. | |
| 2006/0098853 A1 | | 5/2006 | Roundhill et al. | |

(Continued)

FOREIGN PATENT DOCUMENTS

| | | |
|---|---|---|
| JP | 2006-068526 | 3/2006 |
| JP | 2007-068724 | 3/2007 |
| JP | 2009-142335 | 7/2009 |

OTHER PUBLICATIONS

Stephen H. Little, MD, Stephen R. Igob, Bahar Pirat, MD, Marti McCulloch, Craig J. Hartley, PhD, Yukihiko Nosé, MD, PhD, William A. Zoghbi, MD, "In Vitro Validation of Real-Time Three-Dimensional Color Doppler Echocardiography for Direct Measurement of Proximal Isovelocity Surface Area in Mitral Regurgitation", Am J Cardiol. 2007, 99(10), 1442-1447.*

(Continued)

*Primary Examiner* — Tse Chen
*Assistant Examiner* — Lisa Kinnard

(57) ABSTRACT

Volumetric quantification is provided in medical diagnostic ultrasound. By acquiring both B-mode and color flow data without stitching or acquiring in real-time at tens of volumes a second, more reliable quantification may be provided. Using multiple regions of interest in a volume may allow for more accurate and/or complete flow information, such as averaging flow from different locations in the same structure (e.g., use preservation of mass to acquire multiple measures of the same flow).

27 Claims, 4 Drawing Sheets

(56) References Cited

U.S. PATENT DOCUMENTS

| | | | |
|---|---|---|---|
| 2007/0161914 A1* | 7/2007 | Zdeblick et al. | 600/486 |
| 2007/0167771 A1 | 7/2007 | Olstad | |
| 2007/0255136 A1 | 11/2007 | Berg et al. | |
| 2007/0255138 A1 | 11/2007 | Kristofferson et al. | |
| 2008/0051661 A1* | 2/2008 | Kataguchi et al. | 600/455 |
| 2008/0085043 A1 | 4/2008 | Ogasawara et al. | |
| 2008/0167557 A1* | 7/2008 | Kozai | 600/441 |
| 2008/0249411 A1* | 10/2008 | Kye et al. | 600/441 |
| 2009/0003666 A1* | 1/2009 | Wu | 382/128 |
| 2009/0043208 A1* | 2/2009 | Hergum et al. | 600/455 |
| 2009/0062650 A1 | 3/2009 | Miyaki | |
| 2009/0270732 A1 | 10/2009 | Abe et al. | |
| 2009/0306503 A1* | 12/2009 | Srinivasan et al. | 600/441 |
| 2009/0306513 A1* | 12/2009 | Srinivasan et al. | 600/454 |

OTHER PUBLICATIONS

S Little, S Igo, B Pirat, M McCulloch, CJ Hartley, Y Nose, WA Zoghbi, "In Vitro Validation of Real-Time Three-Dimensional Color Doppler Echocardiography for Direct Measurement of Proximal Isovelocity Surface Area in Mitral Regurgitation", 2007, Am J Cardio12007;99: 1440-1447.*

In Vitro Validation of Real-Time Three-Dimensional Color Doppler Echocardiography for Direct Measurement of Proximal Isovelocity Surface Area in Mitral Regurgitation, 2007, Am J Cardiol. 2007;99: 1440-1447.*

Sugeng, et al., *Real-time 3-Dimensional Color Doppler Flow of Mitral and Tricuspid Regurgitation: Feasibility and Initial Quantitative Comparison with 2-Dimensional Methods*, Journal of the American Society of Echocardiography, Sep. 2007, vol. 20, No. 9, pp. 1050-1057, Chicago, IL.

Matsumura, et al., *Determination of Regurgitant Orifice Area with the Use of a New Three-Dimensional Flow Convergence Geometric Assumption in Functional Mitral Regurgitation*, Journal of the American Society of Echocardiography, Nov. 2008, vol. 21, No. 11, pgs. 1251-1256.

Simpson, et al., *Current Status of Flow Convergence for Clinical Applications: Is It a Leaning Tower of "Pisa"?*, JACC, Feb. 1996, vol. 27, No. 2, pgs. 504-509.

Anayiotos, et al., *Morphological Evaluation of a Reguritant Orifice by 3-D Echocardiography: Applications in the Quantification of Valvular Regurgitation*, Ultrasound in Med. & Biol., 1999, vol. 25, No. 2, pp. 209-223.

Coisne, et al., *Quantitative Assessment of Regurgitant Flow with Total Digital Three-Dimensional Reconstruction of Color Doppler Flow in the Convergent Region: In Vitro Validation*, Journal of the American Society of Echocardiography, Mar. 2002, vol. 15, No. 3, pp. 233-240.

Degroot, et al., *Evaluation of 3-D Colour Doppler Ultrasound for the Measurement of Proximal Isovelocity Surface Area*, Ultrasound in Med & Biol., 2000, vol. 26, No. 6, pp. 989-999.

Bargiggia, et al., *A New Method for Quantitation of Mitral Regurgitation Based on Color Flow Doppler Imaging of Flow Convergence Proximal to Regurgitant Oriface*, Circulation vol. 84, No. 4, Oct. 1991, pp. 1481-1489.

Utsunomiya, et al., *Calculation of Volume Flow Rate by the Proximal Isovelocity Surface Area Method: Simplified Approach Using Color Doppler Zero Baseline Shift*, JACC vol. 22, No. 1, Jul. 1993, pp. 277-282.

Pu, et al., *Quantification of Mitral Regurgitation by the Proximal Convergence Method Using Transesophageal Echocardiography*, AHA Circulation © 1995, pp. 2169-2177.

Takashi Sumi, et al., "Mitral Regurgitation: PISA Method" Echocardiography, vol. 10, No. 6, pp. 562-570, 2009, total 12 pages.

English translation of Office Action from counterpart Japanese application No. 2011-40449, drafted Oct. 31, 2014, 7 pages.

* cited by examiner

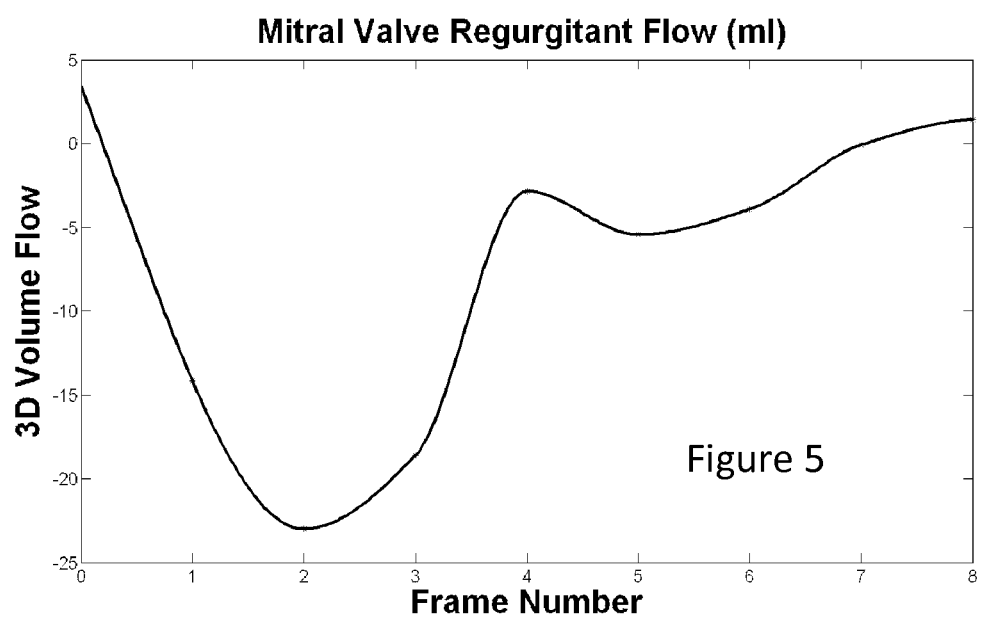

VOLUMETRIC IS QUANTIFICATION FOR ULTRASOUND DIAGNOSTIC IMAGING

BACKGROUND

This present embodiments relates to medical diagnostic ultrasound. In particular, quantification is provided for three- or four-dimensional ultrasound diagnostic imaging.

Color Doppler data representing the heart or other organ of interest may provide useful flow information. For example, valvular regurgitation is an important cause of morbidity and mortality. Doppler echocardiography is a non-invasive technique to evaluate the severity of regurgitation. Several indexes have been developed for two-dimensional echocardiography using Color Doppler, Pulsed wave (PW) and Continuous wave (CW) Doppler. Volume flow may be predicted from modeling of manually segmented color data from two-dimensional images. These two-dimensional methods suffer from limitations of measurements done in a plane, so rely on approximations.

To acquire volumetric flow information, data is acquired over multiple heart cycles and stitched together to form the desired field of view. Stitched acquisition may suffer from inaccuracies caused by beat-to-beat changes in the flow, especially in patients with cardiac arrhythmia. Even where the inaccuracies due to spatial or cyclical variation are minor, various sources of error may result in inaccurate quantification.

BRIEF SUMMARY

By way of introduction, the preferred embodiments described below include a method, system, computer readable medium, and instructions for volumetric quantification in medical diagnostic ultrasound. By acquiring both B-mode and volume color flow data (e.g., full volume) without stitching or in real-time typically at tens of volumes a second, more reliable quantification may be provided. Using multiple regions of interest in a volume may allow for more synchronous, accurate and/or complete flow information, such as averaging flow from different locations in the same structure (e.g. use preservation of mass to acquire multiple measures of the same flow) or using flow information from one or more spatially different locations to correct flow at the location.

In a first aspect, a method is provided for volumetric quantification in medical diagnostic ultrasound. B-mode and flow ultrasound data representing a volume of a patient at a substantially same time are acquired. At least two regions of interest are identified in the volume. The regions of interest are flow regions (e.g., jets, flow tracts, flow surfaces, or vessel lumen) and the identifying is a function of the B-mode and/or flow data. Multi-modality data can be used to complement identification. A flow quantity is calculated as a function of the flow ultrasound data for the at least two regions of interest.

In a second aspect, a computer readable storage medium has stored therein data representing instructions executable by a programmed processor for volumetric quantification in medical diagnostic ultrasound. The storage medium includes instructions for receiving B-mode data and flow data representing a volume at a first time in a first cardiac cycle, identifying a volume region of interest from the B-mode and/or flow data, segmenting a flow structure from the volume region of interest, computing a segment (e.g., a proximal iso-velocity surface area) from the flow data of the flow structure, refining the flow data for the segment (e.g., proximal iso-velocity surface), and calculating a flow quantity or one or more parameters from the refined flow data for the flow segment, the calculating occurring during the first cardiac cycle.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 5 is a graph illustrating one example of a flow quantity as a function of time.

DETAILED DESCRIPTION OF THE DRAWINGS AND PRESENTLY PREFERRED EMBODIMENTS

An automated tool accurately quantifies from volumetric color Doppler data. Real-time volumetric B-mode and color Doppler data is acquired simultaneously over several regions of interest may increase accuracy. Real-time volumetric B-mode and Color Doppler data provides temporally accurate geometry and orientation identification. Anatomic landmarks, such as valves and outflow tracts, are identified with automated flow segmentation. The flow may be subsequently corrected, and volumetric flow quantified for several regions of interest. Spectral Doppler data may be used for de-aliasing color. Flow data may be corrected based on location, geometry, and orientation of the flow data. Based on the segmented anatomy, acquisition can be adapted to improve imaging as well as quantification.

Volumetric flow quantification is obtained by acquisition of real-time volumetric B-mode and flow data and quantification using multiple flow regions of interest, which may include correction or other accuracy improvement. The multiple flow regions of interest may be spatially distinct locations, orientations, planes, or surfaces. Quantification may be performed substantially simultaneously for real-time monitoring and display or on pre-acquired data which accounts for processing delay to calculate from the data as the data is acquired, such as during a same heart cycle or within one or two seconds of completing acquisition.

Improved volume presentation for color flow may reduce the scan-time and improve the work-flow for color flow imaging. Automated identification of image surfaces using the Color flow information may help automated calculations, clinical marker identification, and accurate anatomic representation.

Figure 1:
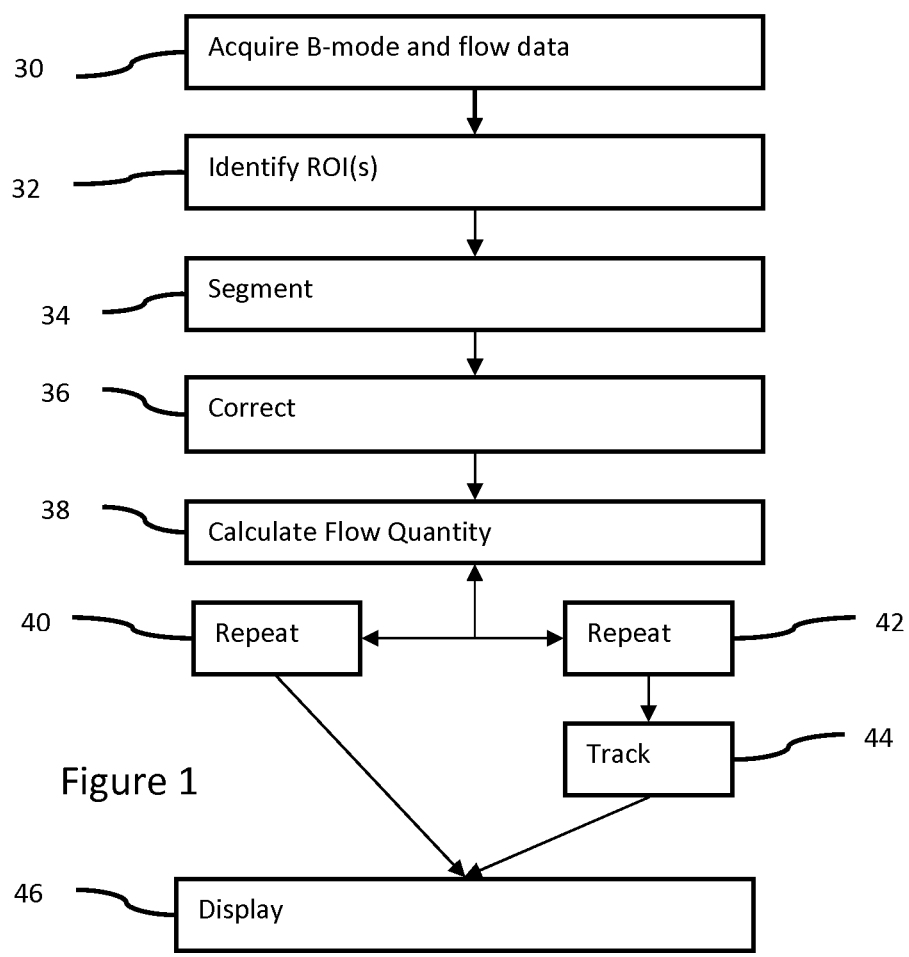
FIG. 1 is a flow chart of one embodiment of a method for volumetric quantification.

FIG. 1 shows a method for volumetric quantification in medical diagnostic ultrasound. The method is performed by the system 10 of FIG. 6 or a different system. The acts of FIG. 1 are performed in the order shown or a different order. Additional, different or fewer acts than shown in FIG. 1 may be used. For example, acts 30, 32, and 38 are performed without any other acts. As another example, act 40 is performed without acts 42 and 44, or vice versa. The acts of FIG. 1, described below, may be implemented in different ways. At least one example embodiment is provided below, but other embodiments are possible.

In act 30, B-mode and flow ultrasound data are acquired. B-mode data represents intensities. Flow data represents estimates of velocity, energy (e.g., power), and/or variance. In one embodiment, at least velocity and energy are estimated. The data is acquired by scanning or from memory. The data is received by scanning or by transfer. In one embodiment, the data is acquired during real-time scanning or as the scanning occurs.

The ultrasound data represents a volume of a patient. The volume is scanned along different planes or other distribution of scan lines within the volume. The scanned volume is an interior of an object, such as the patient. Scanning the volume provides data representing the volume, such as representing a plurality of different planes in the object (e.g., patient or heart). The data representing the volume is formed from spatial sampling of the object. The spatial samples are for locations distributed in an acoustic sampling grid in the volume. Where the acoustic sampling grid includes planar arrangements of samples, the spatial samples of the object include samples of multiple planes or slices.

Spatial samples along one or more scan lines are received. Where the transmit beam insonifies just one receive scan line, then samples along that scan line are received. Where the transmit beam insonifies multiples scan lines, then samples along the multiple scan lines are received. For example, receive beamforming is performed along at least thirty distinct receive lines in response to one broad transmit beam. To generate the samples for different receive beams, parallel receive beamformation is performed so that the different receive beams are sampled at a same time. For example, a system may be capable of forming tens or hundreds of receive beams in parallel. Alternatively, signals received from the elements are stored and sequentially processed.

Spatial samples are acquired for a plurality of receive lines in response to one and/or in response to sequential transmit beams. Using broad beam transmission, spatial samples for multiple thin slices may be simultaneously formed using dynamic receive focusing (e.g., delay and/or phase adjust and sum). Alternatively, Fourier or other processing may be used to form the spatial samples.

The scanning may be performed a plurality of times. The acts are repeated to scan sequentially different portions of the field of view. Alternatively, performing once acquires the data for the entire field of view.

The complete volume is scanned at different times. Scanning at different times acquires spatial samples associated with flow. Any now known or later developed pulse sequences may be used. A sequence of at least two (flow sample count) transmissions is provided along each scan line. Any pulse repetition frequency, ensemble/flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be wall filtered/clutter filtered. The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

Flow data is generated from the spatial samples. Any flow data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. Color is used to distinguish from spectral Doppler imaging, where the power spectrum for a range gate is estimated. The change in frequency between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time. Multiple frames of flow data may be acquired to represent the volume at different times.

The estimation is performed for spatial locations in the volume. For example, velocities for the different planes are estimated from echoes responsive to the scanning.

The estimates may be thresholded. Thresholds are applied to the velocities. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

B-mode data is also acquired. One of the scans used for flow data estimation or a different scan is performed. The intensity of the echoes is detected for the different spatial locations.

For the volume, some spatial locations are represented by B-mode data and other locations are represented by flow data. Thresholding or another process is performed to avoid a location being represented by both B-mode and flow data. Alternatively, one or more locations may have values for both B-mode and flow data. While both types of data together represent the volume, the different types of data may be separately stored and/or processed or may be merged into one set representing the volume.

By using broad beam transmit and receiving along a plurality of scan lines or otherwise acquiring the data for a larger sub-volume or entire volume for each transmission, more rapid scanning is provided. The more rapid scanning may allow for real-time acquisition of B-mode and color Doppler estimates. For example, the volume is scanned at least 10 times a second. In one embodiment, the volume rate is 20, 25 or other numbers of volumes per second. Each volume scan is associated with acquiring both B-mode and Doppler data. The different types of data are acquired at a substantially same time. Substantially allows for interleaving of different transmissions and/or receive processing for the different types of data. For example, ten or more volumes of data are acquired each heart cycle where each volume includes B-mode and velocity data representing a generally same portion (e.g., within 1/10$^{th}$ of the heart cycle of each other) of the heart cycle. In alternative embodiments, the rate of acquisition for B-mode data is greater than or less than for color flow data.

In act 32, a volume region of interest is identified from the data. The region of interest is a tissue or flow region of interest. For example, the B-mode data is used to identify a tissue structure, such as a valve or heart wall. The region of interest is positioned over, adjacent to, or at a location relative to the tissue structure. For example, a valve is located. A flow region of interest spaced from the valve to cover a jet region is identified based on the location of the valve. A flow region may include a jet, flow tracts, flow surfaces, or vessel lumen. Since the flow and B-mode data are acquired at substantially the same time, the data is spatially registered and one type of data may be used to determine a region associated with another type of data. Alternatively, the volume region of interest is identified from the flow data without B-mode information, such as identifying a jet region, jet orientation or turbulent flow.

The identification is manual, semi-automated, or automated. The user may position, size and orient the region of interest. A processor may apply any algorithm to determine the region of interest, such as a knowledge-based, model, template matching, gradient-based edge detection, gradient-based flow detection, or other now known or later developed tissue or flow detection. For semi-automated identification, the user may indicate a tissue structure location, edge point, or other information used by a processor to determine the location, orientation, and size of the region of interest.

Figure 2:
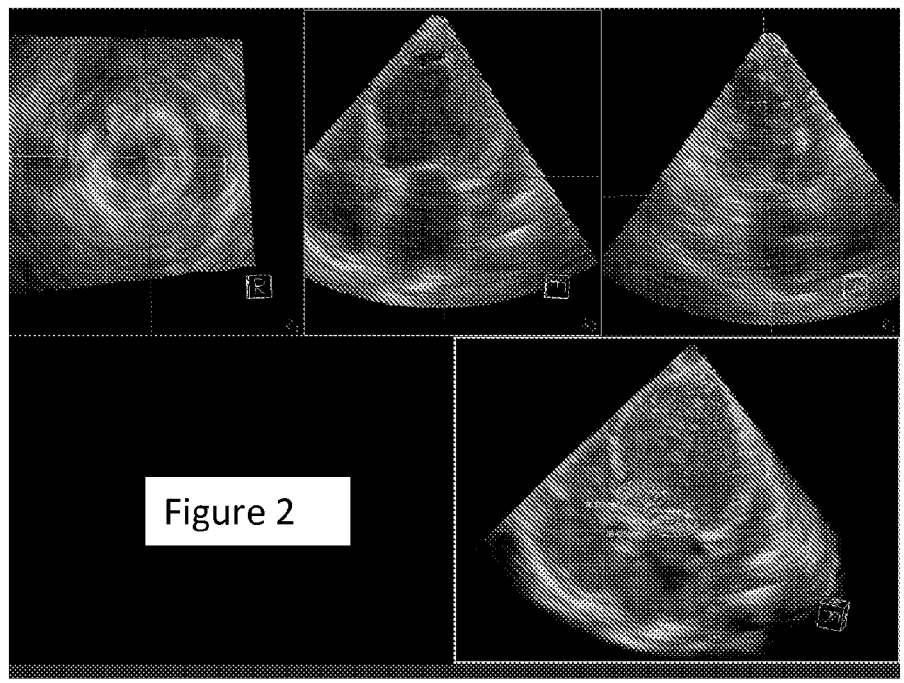
FIG. 2 shows example medical diagnostic ultrasound images of the heart with multiple regions of interest.

More than one volume region of interest may be identified. The regions of interest are identified in the same volume. For example, two flow regions of interest are identified. The flow region may be such that flow is accurate in one region and it is used to de-alias flow in the other region. The flow regions of interest are associated with conservation of mass, such as being part of a same vessel, chamber, or other flow structure. In one embodiment, a region of interest associated with a jet for a valve is identified, and a region of interest associated with an outflow tract is identified. The instantaneous flow from one region may be used to correct flow in the other region of interest based on but not limited to computation of overall volume change of the heart cavity from the previous instance. For example, FIG. 2 shows two regions of interest positioned in a three-dimensional rendering of the volume. The center, upper image is a planar reconstruction of an A4C view. The upper-left image is looking downward from the apex of the A4C view. The upper right image is an A2C view substantially orthogonal to the A4C view. For the three-dimensional rendering, about ½ the volume is masked such that the rendering is of half the volume with the A4C plane as a front face orthogonal to the viewing direction. The regions of interest identify the Left Ventricle Outflow tract (LVOT) and Mitral valve annulus. Flow regions associated with other structures may be identified.

The regions of interest are spatially distinct. For overlapping or for entirely spatially distinct regions of interest, some locations in one region of interest are not in another region of interest and some locations of the other region of interest are not in the one region of interest. FIG. 2 shows the regions of interest as entirely distinct or without any overlap.

In other embodiments, the different regions of interest are associated with a same tissue or flow structure. For example, two different areas in a same jet are identified. As another example, two different surfaces associated with different velocities but a same flow region are identified. In yet another example, two flow regions on opposite sides of a tissue structure, such as a valve, are identified. The regions of interest may be in the same flow tract to provide multiple measurements of the same flow at different locations. The regions may serve as location for additional measurement, such as PW measurement, and their known spatial location and orientation with respect to the flow anatomy may be used to correct flow estimation. The position may allow measurement after turbulence inducing regions, such as along a curved structure. The curvature may change with time, making one measure more accurate than another and vice versa at different times.

The region of interest has any desired shape. For example, a sphere, cube, planar, three-dimensional surface, or other shape is used. In one embodiment, a conical shape is used. The narrow portion of the conical shape is at a narrower flow region, such as adjacent a valve, orifice, or hole in the heart wall. The wider portion of the conical shape is spaced away to better cover the diverging flow caused by turbulence. The shape may be directional. By orienting the region of interest based on the flow, such as the direction of flow, axial velocities may be angle corrected.

The region of interest is identified in one volume or time instance. For other volumes in a sequence, the region may be independently identified or identified based on a previous location (e.g., tracking of the region).

In act 34, the flow and anatomical information in one or more regions of interest are segmented. Where flow is being quantified, the segmentation may remove information from tissue. The flow structure is segmented from the volume of interest. In each region of interest, anatomical and flow structures, such as flow tract, B-mode walls, valves, jets, and flow-contours are segmented.

The segmentation is manual, semi-manual, or automated. The user may manually indicate the locations of flow and/or tissue. A processor may apply any algorithm to segment, such as a knowledge-based, model, template matching, gradient-based edge detection, gradient-based flow detection, or other now known or later developed tissue or flow detection. For example, the threshold process to determine whether sufficient flow exists in combination B-mode and color Doppler images is used. The B-mode, velocity, energy, and/or other information are thresholded. Locations with large B-mode or small velocity and/or energy are indicated as tissue. Locations with small B-mode or sufficient velocity and/or energy are indicated as flow. In one embodiment, the data for the region of interest is low pass filtered. Gradients of the filtered B-mode data are used to determine a tissue border. The border separates tissue from flow structure. Other edge detection may be used, such as gradient of flow data to better isolate the flow of interest. Combinations of both may be used.

Figure 3:
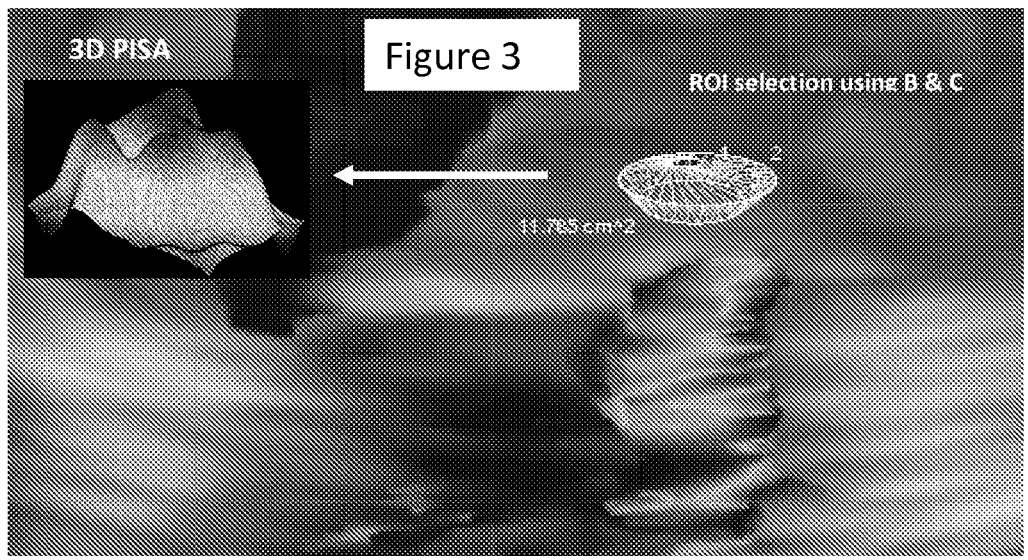
FIG. 3 shows example medical diagnostic ultrasound images associated with extraction of a proximal iso-velocity surface area associated with a region of interest.

In one embodiment, the segmentation of act 34 determines a specific flow structure from a sub-set of the flow portion of the region of interest. For example, the location of a proximal iso-velocity surface area (PISA) is computed from the flow data of the flow structure. FIG. 3 represents an example segmentation of a PISA for one region of interest. The PISA is a three-dimensional iso-velocity contour. The contour is a surface with the same or similar velocity across the flow region. The surface may be spatially filtered. The PISA surface in FIG. 3 is for a patient with mitral regurgitation. The PISA may be displayed or used without display.

Any velocity may be used and more than one surface may be determined by using multiple velocities on the same jet. In other embodiments, multiple such surfaces may be used simultaneously on more than one valve and spatially distinct locations. The segmentation may be performed for multiple aliasing velocities. By using more than one segmentation, multiple flow regions of interest are identified as PISA in a same or different larger region of interest. The multiple flow regions may be used to determine a more accurate assessment of a quantity or parameter, such as an overall effective regurgitant orifice area (EROA) calculation made as an average of multiple automated measurements.

The velocity data may be low pass filtered prior to segmentation. Ranges of velocities may be used to determine a surface with depth.

In act 36, the flow ultrasound data associated with the segmented flow region and/or the volume of interest may be corrected. Correction includes alteration of the data and/or verification where lack of verification leads to correction by reacquisition. The correction occurs prior to calculating quantities. In the order shown, correction occurs after segmentation. In other embodiments, correction occurs prior to identification of act 32 or after identification but prior to segmentation of act 34. In yet other embodiments, correction is performed on the quantity determined in act 38 rather than or in addition to correction prior to calculation of the quantity.

Velocity data may be refined by anti-aliasing. Any anti-aliasing approach may be used. For example, a CW or PW measurement is performed to determine a maximum velocity. The gate location is placed manually or automatically. For automatic placement, the gate is located at the location of maximum velocity in the segmented flow. Velocities associated with a large gradient near the maximum of the velocity scale but less than the PW or CW maximum velocity may be unaliased.

Velocity data may be refined by angle correction. The position of the region of interest and/or the segmented flow data may indicate a direction of flow. The axial velocity may be increased to account for the difference in angle between the scan line and the actual direction of flow.

The flow data may be compared to a template or thresholds. For example, an average velocity is determined. If sufficiently deviant, then the region of interest may be repositioned in an attempt to better isolate the flow of interest. Alternatively, a region determined from a volume at a previous time (e.g., immediately prior volume or volume from the same phase of the heart cycle) may be used as a replacement.

In one embodiment, multiple corrections are performed. For example, the flow data for the proximal iso-velocity surface is refined. The velocity estimates are unaliased and angle corrected in the volume region of interest if the velocity data indicates abrupt change in sign or absence of flow on voxel by voxel or groups of voxel basis. A model for iso-velocity surface or cross-sectional flow may be used to assist in correction on voxel by voxel basis. The velocity estimation is corrected based on a PW estimate of flow and multiple estimations of flow for any cross section or PISA. De-aliasing, angle correction, computation of Reynolds number, velocity interpolation and/or correction based on an expected profile estimated for a Reynolds number may be used. For example, the Reynolds number may indicate insufficient or too much turbulence. The Reynolds number is determined from a flow area (e.g., diameter), velocity of flow, viscosity of blood, and blood density. The Reynolds number may be used to select a model to be used for calculation.

In another embodiment, the proximal iso-velocity surface is refined by determining such surfaces for a plurality of settings. Where the velocity for defining the surface is sufficiently low, flow regions may be missing and the surface is discarded. For other surfaces, the average area may be used. The area may be similar for the same flow structure but different velocities. Using an average area, a more robust estimate of effective regurgitant orifice area (EROA) may be obtained.

In another embodiment, a volume integral of a flow parameter (such as velocity) is computed within the anatomically-relevant period of interest (like a heart cycle). The anatomically-relevant period of interest may be a heart cycle, breathing cycle, flow-in, out-flow, or other period.

In another embodiment, flow statistics, such as mean or max or variance or spatial and temporal gradient, are computed from within a volume or an iso-surface area, such as equal velocity or equal energy, within the anatomically-relevant period of interest (like a heart cycle).

In act 38, a quantity is calculated. The quantity is a flow quantity, tissue quantity or other type of value, such as the EROA. The quantity is calculated from the flow ultrasound data, the B-mode data, spectral Doppler data (CW or PW), other types of data, or combinations thereof.

The quantity is determined for a given time, such as associated with a volume. The time may be any point in the heart cycle or a specific point in the heart cycle (e.g., volume at diastole or systole). The same quantity may be calculated multiple times, such as at different times in different heart cycles or a same heart cycle. The results may be kept separate, combined (e.g., averaged), filtered or otherwise processed. In alternative embodiments, the quantity is calculated from data at different times, such as determining a difference between two volumes at two different times. The quantity may be calculated over one or more heart cycles.

In a real-time implementation, at least one of the quantities is calculated during a same heart cycle as the acquisition of act 30. Before a complete heart cycle occurs after acquisition of the volume, the quantity is calculated. The calculation occurs during the cardiac cycle. Greater or lesser delay may be provided. The calculation is performed during acquisition, even if not within a heart cycle. The calculation is part of the on-going diagnostic examination or scan session. In alternative embodiments, the calculation is performed for data acquired during a different hour, day or other time, such as during a review session after an examination or scan session.

The quantity is calculated from data of one or more regions of interest. The same or different quantity may be calculated for each region of interest. The calculations may be independent, such as the data and/or quantity for one region of interest not being used or a factor in the calculation of the quantity for another region of interest.

In one embodiment, the quantities from different regions of interest are related. A quantity is determined from information for two or more regions of interest. The quantity is a function of or combination of data, quantities, or other derived information from more than one region of interest.

For flow quantities, multiple regions of interest may be used in combination based on maintaining preservation of mass. The flow may be along a flow tract, such as a vessel or heart chamber. By positioning the regions of interest at different locations, the relationship of flow between the locations may be determined. The same quantity may be calculated at different locations and averaged where the quantities should be the same. This may provide a more robust or accurate estimate than using one region. In one example, the regions of interest are at multiple cross sectional planes or surfaces in a jet (e.g., multiple regions corresponding to different PISA in a same jet or outflow). In another example, the regions are at two locations spaced apart by a region of change, such as one at a valve and another at an outflow tract, on opposite sides of a bend in a vessel, at different locations along a vessel, or at different valves or locations in a heart chamber.

Using preservation of mass for flow occurring simultaneously in two distinct locations (e.g. LVOT and Mitral regurgitation (MR)), correction rather than just averaging may be used. The change in net volume of the ventricle during contraction divides flow between the LVOT and MR. The flow is corrected simultaneously at two distinct locations. The angle between the two regions changes with time, so angle correction of the flow may be performed on the data of one region of interest based on the changing orientation of the relative regions of interest and the scan line direction.

Preservation of mass may be used for flow along any arbitrary surface, such as an anatomical structure or just a flow structure (PISA). A combination of estimation of flow using an ROI (PISA, which is a flow structure) and LVOT (which is an anatomical structure) may be used for instantaneous flow estimation and correction.

Instantaneous flow estimation could be performed on a flow structure (PISA) and can be used to correct/estimate flow in a separate downstream flow ROI, such as in the jet.

The quantity may be a PW estimate. By placing regions of interest at a vessel bifurcation or other branching, the orientation of flow may be tracked for angle correcting the PW estimate. The flow in a main branch may be determined from the sum of flows in the bifurcations.

Any quantity may be calculated, such as a maximum velocity, minimum velocity, average velocity, area, volume, or other value. In one embodiment, the proximal iso-velocity surface area is calculated. The corrected flow data output from act 36 is used to determine the PISA. The maximum, minimum, average, area, perimeter, velocity area integral or other value related to the PISA is determined. These quantities indicate flow in any cross section in the anatomy or flow structure of interest. The velocity area over time may be integrated. In one embodiment, flow in three-dimensions is quantified as the effective regurgitant orifice area (EROA). EROA is the surface area of the PISA multiplied by the aliasing velocity and divided by the peak velocity. The peak velocity may be determined from Doppler estimates or from a CW or PW (spectral Doppler) analysis.

The PISA related quantity may be calculated at different regions of interest, such as at different aliasing velocities for the same flow structure. The PISA surface is defined by the velocity. By determining different PISA for different velocities, different velocity cross-section regions of interest are used. The results from the multiple regions may be averaged.

Figure 4:
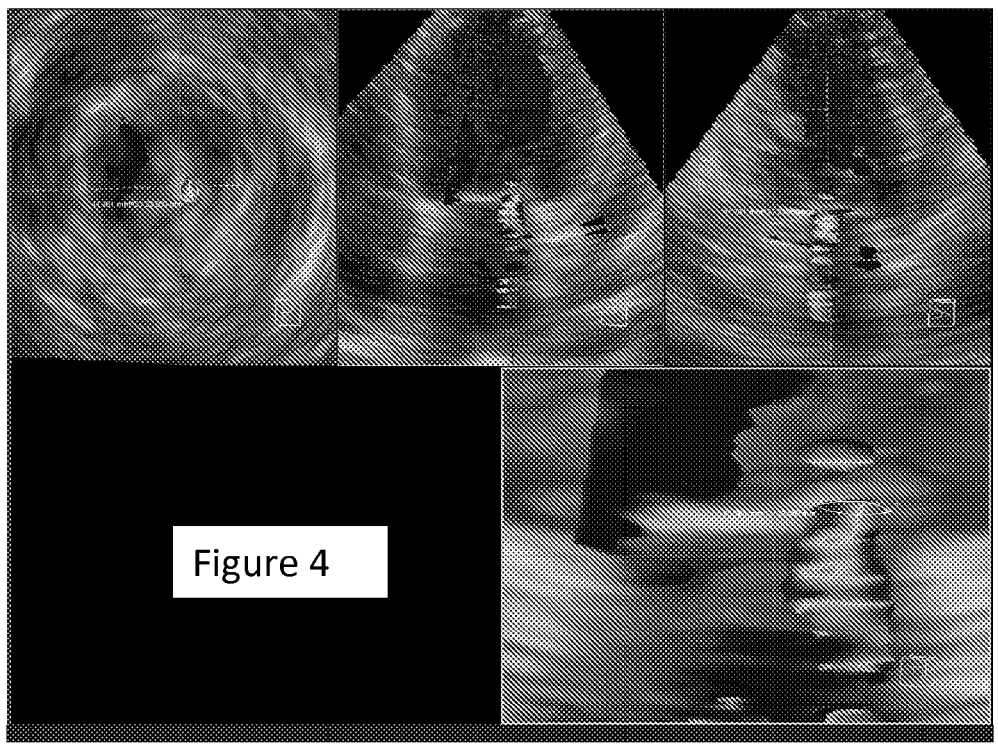
FIG. 4 shows example medical diagnostic images with segmented information based on both B-mode and color Doppler information.

The results may be displayed with images. For example, FIG. 4 shows segmentation based on three-dimensional B-mode and color Doppler data. The vena contract location and orientation are shown below the valve coaptation line. The area of vena contracta and perimeter is shown in the volume rendered image. The flow related parameters are computed and displayed with visualization of location and orientation of the flow anatomy (e.g., vena contracta cross section in this case).

In act 40, the acquisition of act 30 is repeated. A sequence of volumes is acquired, such as volumes over one or more heart cycles. The quantity calculation of act 38 may use data from different times to determine the quantity. In one embodiment, a temporal flow parameter representing flow over a heart cycle or portion of a heart cycle is calculated. The temporal flow parameter is calculated as a function of the flow data for the region of interest throughout the sequence. Example temporal flow parameters include stoke volume, regurgitant volume, or flow rate from the time sequence.

In act 42, the acquisition of act 30 and the calculation of act 38 are repeated. For example, the repetition occurs multiple times in a same heart cycle. A sequence of volumes is acquired. The same quantity is calculated for different times, such as for each volume, throughout a portion of a cycle or an entire cycle.

The regions of interest may be assumed to be in the same locations. Alternatively, acts 32, 34, and 36 may be repeated as well. In another alternative, tracking is performed in act 44. One or more regions of interest are tracked through the sequence. A similarity calculation may be used to determine a best fit location and orientation for a region of interest in other volumes. The correlation, minimum sum of absolute differences or other similarity calculation is performed. The B-mode data is used to track. Alternatively, flow data is used. Both B-mode and flow data may be used, such as tracking with both and averaging the location. The quantity is calculated for each volume from the tracked region of interest.

In act 46, the quantity is displayed with or without images. The quantity is displayed as a value, number, graph, color modulation, or text. As a sequence of images is viewed, the quantities associated with the given volume or data is displayed. As shown in FIG. 4, the quantity or quantities associated with the volume and/or heart cycle are displayed as well as an indication of the region of interest. As shown in FIG. 3, the PISA associated with each volume may additionally or alternatively be displayed.

In one embodiment, a graph of the flow quantity may be output. The graph is of the quantity as a function of time, such as throughout one or more cardiac cycles. The graph is displayed during the acquiring, such as during a same heart cycle or imaging session. FIG. 5 shows an example graph. The results of flow computation from three-dimensional color Doppler data based on a three-dimensional ROI over a mitral regurgitant jet is shown in FIG. 5. Instantaneous flow is computed for each frame or volume, and the summation of instantaneous flow measurement provides the net flow in the jet. No geometric assumption of the flow tract or anatomy is necessary or used in this computation. Several ROIs may be used to obtain a robust estimate of flow based on the preservation of mass principle.

Other acts may be provided. For example, the scanning conditions may adapt based on the quantity. The PW scale, color scale, or color acquisition parameters may adapt based on the quantity. For example, the PISA may be flat or unusual due to aliasing. If the PISA is flat or associated with a quantity or quantities in a particular pattern, the velocity scale may be adjusted. The Doppler window, scale, parameters (e.g., wall filter type), thresholds (e.g., wall filter thresholds), and pulse repetition frequency (PRF) interactively or automatically adapt to optimize the acquisition for the anatomy of interest (or flow structure). The adaptation may result in a greater or maximum number of estimations or improve accuracy.

Figure 6:
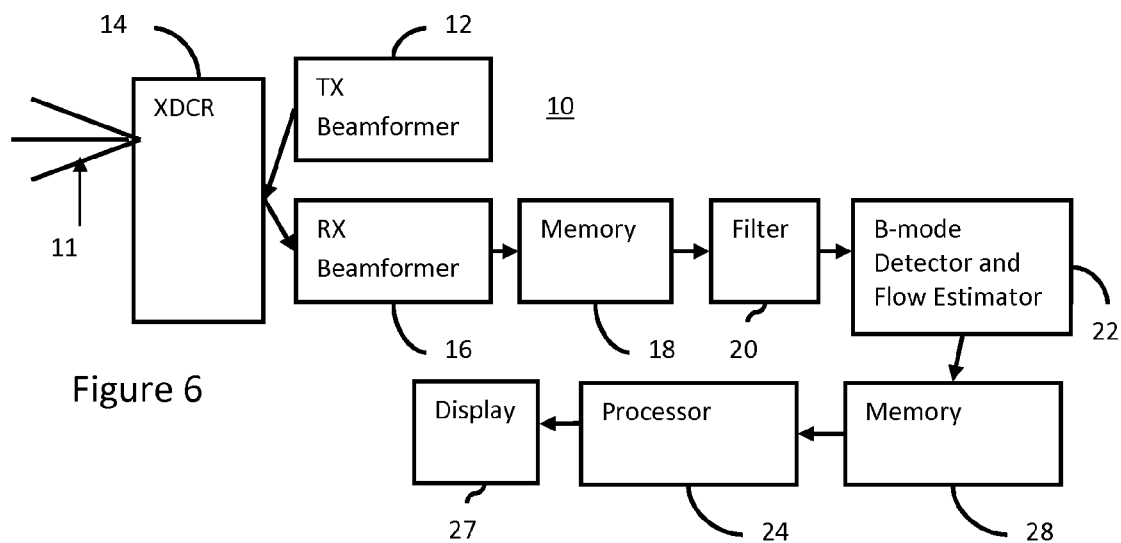
FIG. 6 is a block diagram of one embodiment of a system for volumetric quantification.

FIG. 6 shows one embodiment of a system 10 for volumetric quantification in medical diagnostic ultrasound. The system 10 includes a transmit beamformer 12, a transducer 14, a receive beamformer 16, a memory 18, a filter 20, a B-mode detector and flow estimator 22, a memory 28, a processor 24, and a display 27. Additional, different or fewer components may be provided. For example, the system includes the B-mode detector and flow estimator 22 and processor 24 without the front-end components, such as the transmit and receive beamformers 12, 16. In one embodiment, the system 10 is a medical diagnostic ultrasound system. In an alternative embodiment, the system 10 is a computer or workstation. In yet another embodiment, the B-mode detector and flow estimator 22 are part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. In one embodiment, the transmit beamformer 12 transmits beams sufficiently large to cover at least thirty distinct receive lines, and the receive beamformer 16 receives along these distinct receive lines in response to the transmit beam. Use of the broad beam transmit and parallel receive beamforming along tens or hundreds of receive lines allows for real-time scanning of multiple slices or a volume. The receive lines and/or transmit beams are distributed in the volume, such as the receive lines for one transmit being in at least two different planes. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more (e.g., 30, 40, or 50) receive beams in response to each transmit beam. The receive beams are collinear, parallel and offset or non-parallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for a substantially same spatial location. Phase changes between the different receive events indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a three-dimensional grid.

The filter 20 is a clutter (e.g., wall) filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 identifies velocity information from slower moving tissue as opposed to fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The B-mode detector and flow estimator 22 is a Doppler processor or cross-correlation processor for estimating the flow data and a B-mode detector for determining the intensity. In alternative embodiments, another device now known or later developed for estimating velocity, energy, and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The energy and variance may also be calculated.

Flow data (e.g., velocity, energy, or variance) is estimated for spatial locations in the scan volume from the beamformed scan samples. For example, the flow data represents a plurality of different planes in the volume.

The flow estimator 22 may apply one or more thresholds to identify sufficient motion information. For example, velocity and/or energy thresholding for identifying velocities is used. In alternative embodiments, a separate processor or filter applies thresholds. The B-mode detector and flow estimator 22 outputs B-mode and flow data for the volume.

The memory 28 is video random access memory, random access memory, removable media (e.g. diskette or compact disc), hard drive, database, or other memory device for storing B-mode and flow data. The stored data is in a polar or Cartesian coordinate format. The memory 28 is used by the processor 24 for the various filtering, rendering passes, calculations or other acts described for FIG. 1. The processor 24 may additionally reformat the data, such as interpolating the data representing the volume to a regularly spaced Cartesian coordinate three-dimensional grid.

The display 27 is a CRT, LCD, plasma, projector, monitor, printer, touch screen, or other now known or later developed display device. The display 27 receives RGB or other color values and outputs an image. The image may be gray scale or color image. The image represents the region of the patient scanned by the beamformer and transducer 14.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 operates pursuant to instruction provided in the memory 18, 28, or a different memory for adaptive volume rendering in medical diagnostic ultrasound.

The processor 24 receives B-mode and flow data from the B-mode detector and flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 calculates one or more quantities and causes generation of an image as a two-dimensional image representing a volume from a viewing direction. The image is rendered from B-mode and flow data. The rendering is performed using rendering parameters. One or more of the rendering parameters may have adaptive values. For example, the values are different for different locations. Along a ray line for rendering, the opacity and/or fade may have different values depending on the B-mode and flow data along the ray line.

The instructions for implementing the processes, methods and/or techniques discussed above are provided on computer-readable storage media or memories, such as a cache, buffer, RAM, removable media, hard drive or other computer readable storage media. In one embodiment, the instructions are for volumetric quantification. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for volumetric quantification in medical diagnostic ultrasound, the method comprising:
   acquiring B-mode and flow ultrasound data representing a volume of a patient at a substantially same time;
   identifying at least two regions of interest in the volume, the at least two regions of interest being flow regions for the flow ultrasound data after thresholding the identifying being a function of both B-mode and flow data, the at least two regions of interest being for different spaced apart structures of the patient;
   segmenting a distributed flow structure having a three-dimensional contour of a surface defined by a range of velocities in each of the at least two regions of interest, the range of velocities being for the flow ultrasound data after thresholding;
   spatially filtering the surface; and
   calculating a flow quantity value as a function of the spatially filtered flow structure for more than one of the at least two regions of interest.

2. The method of claim 1 wherein one of the at least two regions of interest is a conical region adjacent a heart valve, the conical region being less than half of the volume represented by the B-mode data.

3. The method of claim 1 wherein acquiring comprises acquiring with a volume frame rate of at least 10 per second including scans for both the B-mode and flow ultrasound data.

4. The method of claim 1 wherein calculating comprises calculating as a function of the flow structure using data distributed in three dimensions, the calculating occurring during a same heart cycle of the patient as the acquiring of the data from the patient.

5. The method of claim 1 further comprising repeating the acquiring and calculating and displaying a graph of the flow quantity as a function of time during the acquiring.

6. The method of claim 1 wherein calculating the flow quantity comprises calculating a proximal iso-velocity surface area within a same physiologically-relevant period of interest as the acquiring.

7. The method of claim 1 wherein identifying comprises identifying the at least two regions of interest as spatially distinct such that first locations in the volume in a first of the at least two regions of interest are not in a second of the at least two regions of interest and such that second locations in the volume in the second region of interest are not in the first region of interest.

8. The method of claim 7 wherein the first and second regions of interest are free of overlap.

9. The method of claim 7 wherein the first and second regions of interest comprise different areas associated with the different ranges of velocities, and the calculating comprises calculating the flow quantity as for spatially filtered iso-velocity surfaces for a same flow structure at the different ranges of velocities and averaging values calculated from the spatially filtered iso-velocity surfaces.

10. The method of claim 1 further comprising:
segmenting flow and anatomical information for the at least two regions of interest.

11. The method of claim 1 further comprising:
correcting the flow ultrasound data prior to calculating.

12. The method of claim 11 where correcting comprises velocity angle correction, velocity aliasing correction, wall-filter cut-off compensation, or combinations thereof.

13. The method of claim 1 wherein calculating comprises calculating an effective regurgitant orifice area.

14. The method of claim 1 further comprising repeating the acquiring, and tracking the at least two regions of interest through a sequence of the B-mode, flow ultrasound or both B-mode and flow ultrasound data;
wherein calculating comprises calculating the flow quantity as a temporal flow parameter representing flow over a heart cycle.

15. The method of claim 1 wherein calculating the flow quantity comprises calculating a volumetric surface or volume integral within a same physiological period of interest of the patient as the acquiring of the data used for the calculating from the patient.

16. The method of claim 1 wherein calculating the flow quantity comprises calculating flow statistics from a volumetric iso-surface area or a sub-volume within a same physiologically-relevant period of interest of the patient as the acquiring of the data used for the calculating from the patient.

17. In a non-transitory computer readable storage medium having stored therein data representing instructions executable by a programmed processor for volumetric quantification in medical diagnostic ultrasound, the storage medium comprising instructions for:
receiving B-mode data and flow data representing a volume at a first time in a first cardiac cycle of the patient;
identifying a volume region of interest from the B-mode data;
segmenting a volumetric flow structure from the volume region of interest, the flow structure comprising a three-dimensional structure of flow separate from tissue;
computing a first volumetric region of interest from the flow data of the volumetric flow structure;
refining the flow data for the first volumetric region of interest; and
calculating a flow quantity from the refined flow data representing spatial locations distributed in three-dimensions for the first volumetric region of interest, the calculating occurring in real time during the first cardiac cycle of the patient as occurring in the patient.

18. The non-transitory computer readable storage medium of claim 17 wherein calculating the flow quantity comprises calculating a perimeter, area, or velocity area integral of a proximal iso-velocity surface area.

19. The non-transitory computer readable storage medium of claim 17 wherein the flow data comprises velocity estimates and wherein refining comprises unaliasing the velocity estimates, angle correcting the velocity estimates, or moving the volume region of interest.

20. The non-transitory computer readable storage medium of claim 17 wherein identifying comprises identifying a conical region of interest adjacent to a heart valve or heart wall orifice, the conical region being less than half of the volume represented by the B-mode data.

21. The non-transitory computer readable storage medium of claim 17 further comprising repeating the receiving and calculating a plurality of times during the first cardiac cycle and outputting a graph of the flow quantity as a function of time throughout the first cardiac cycle.

22. The non-transitory computer readable storage medium of claim 17 further comprising repeating the receiving a plurality of times during the first cardiac cycle as a sequence and wherein calculating comprises calculating a temporal flow parameter as a function of the flow data for the region of interest throughout the sequence.

23. The non-transitory computer readable storage medium of claim 17 further comprising identifying another volume region of interest spatially distinct from the volume region of interest, and wherein calculating comprises calculating as a function of flow data for the volume region of interest and the other volume region of interest.

24. The method of claim 1 wherein identifying comprises identifying the at least two regions of interest as associated with different spaced apart structures comprising different tissue structures.

25. The method of claim 24 wherein identifying comprises identifying the at least two regions of interest as associated with different flow regions in a same flow tract.

26. The method of claim 1 wherein identifying comprises identifying a spatial distribution of different areas of different velocities in a same flow region.

27. The method of claim 1 wherein calculating the flow quantity comprises calculating a proximal iso-velocity surface area for a first of the at least two regions and calculating a flow quantity from flow ultrasound data in a second of the at least two regions.

* * * * *